US010391134B2

(12) United States Patent
Meuwly et al.

(10) Patent No.: US 10,391,134 B2
(45) Date of Patent: Aug. 27, 2019

(54) ANTI-CANDIDA COMPOSITIONS AND USES THEREOF

(71) Applicant: PharmAlp SA, Conthey (CH)

(72) Inventors: Philippe Meuwly, Aubonne (CH);
Christian Abbet, Massongex (CH);
Bruno Schnyder, Crans (CH);
Jean-Martin Denis, Conthey (CH);
Xavier Simonnet, Fully (CH)

(73) Assignee: PHARMALP SA, Conthey (CH)

( * ) Notice: Subject to any disclaimer, the term of this patent is extended or adjusted under 35 U.S.C. 154(b) by 278 days.

(21) Appl. No.: 15/305,591

(22) PCT Filed: Apr. 23, 2015

(86) PCT No.: PCT/IB2015/052963
§ 371 (c)(1),
(2) Date: Oct. 20, 2016

(87) PCT Pub. No.: WO2015/162579
PCT Pub. Date: Oct. 29, 2015

(65) Prior Publication Data
US 2017/0035821 A1 Feb. 9, 2017

(30) Foreign Application Priority Data

Apr. 24, 2014 (EP) .................................... 14165729

(51) Int. Cl.
*A61K 36/185* (2006.01)
*A61K 9/00* (2006.01)
*A61K 36/282* (2006.01)
*A61K 9/08* (2006.01)
*A61K 35/741* (2015.01)
*A61K 35/00* (2006.01)

(52) U.S. Cl.
CPC .......... *A61K 36/185* (2013.01); *A61K 9/0034* (2013.01); *A61K 9/0053* (2013.01); *A61K 9/08* (2013.01); *A61K 35/741* (2013.01); *A61K 36/282* (2013.01); *A61K 2035/115* (2013.01); *A61K 2236/00* (2013.01); *A61K 2236/333* (2013.01); *A61K 2236/51* (2013.01); *A61K 2236/53* (2013.01)

(58) Field of Classification Search
CPC ..................................................... A61K 36/00
USPC ....................................................... 424/725
See application file for complete search history.

(56) References Cited

U.S. PATENT DOCUMENTS

2007/0269537 A1  11/2007  Gupta

FOREIGN PATENT DOCUMENTS

WO   WO-2008/030536 A2   3/2008

OTHER PUBLICATIONS

Abbet et al., 2014, "Comprehensive Analysis of Cirsium Spinosissimum Scop., A Wild Alpine Food Plant" Food Chemistry, 160 (1), 165-170.
Anti-blister Stick, Mintel; Nov. 2008 (Nov. 2008), www.gndp.com.
Bassetti et al., 2010, "Bench-to-Bedside Review: Therapeutic Management of Invasive Candidiasis in the Intensive Care Unit" Critical Care, 14 (6), 244.
Battinelli et al., 2001, "Antimicrobial Activity of *Epilobium* spp. Extracts" 2001, il farmaco, 56(5-7), 345-348.
Bennett et al., 2005, "Mating in Candida Albicans and the Search for a Sexual Cycle" Annu. Rev. Microbiol., 59, 233-255.
Choo et al., 2010, "A Comparative Histopathological Study of Systemic Candidiasis in Association with Experimentally Induced Breast Cancer" Oncology Letters, 1(1), p. 215-222.
Ducrey et al., 1995, "Analysis of Flavonol Glycosides of Thirteen *Epilobium* Species (Onagraceae) by LC-UV and Thermospray LC-MS" Phytochemistry, 38(1), 129-137.
Ducrey et al., 1997, "Inhibition of 5a-Reductase and Aromatase by the Ellagitannins Oenothein A and Oenothein B from *Epilobium* Species" Planta Med, 63(2), 111-114.
Egan et al., 2000, "Diagnosis of Vaginitis" Am. Fam. Physician, 62(5), 1095.
European Search Report for corresponding EP Application 14165729.6 dated Sep. 30, 2014.
Foxman B, 1990, "The Epidemiology of Vulvovaginal Candidiasis: Risk Factors" Am. J. Public Health, 80 (3), 329.
Geiger et Foxman, 1996, "Risk Factors for Vulvovaginal Candidiasis: A Case Control Study Among University Students" Epidemiology, 7(2), 182.
Hevesi et al., 2009, "Antioxidant and Antiinflammatory Effect of Epilobium Parviflorum Schreb." Phytotherapy Research, 23, (5), 719-724.
Ilkit et al., 2011, "The Epidemiology, Pathogenesis, and Diagnosis of Vulvovaginal Candidosis: A Mycological Perspective" Critical reviews in microbiology, 37 (3), p. 250-261.
International Search Report and Written Opinion for PCT/IB2015/052963, dated Sep. 28, 2015.
Kiss et al., 2011, "Oenothein B's contribution to the Anti-Inflammatory and Antioxidant Activity of *Eplilobium* sp." Phytomedicine, 18(7), 557-560.
Monif, 1985, "Classification and Pathogenesis of Vulvovaginal Candidiasis" Am. J. Obstet. Gynecol., 152(7) 935.
Odds, 1987, "Candida Infections: An Overview" Crit. Rev. Microbiol., 15 (1):1-5.
Ollert et al., 1993, "Mechanisms of Adherence of Candida Albicans to Cultured Human Epidermal Keratinocytes." Infection and Immunity, 61 (11), 4560).
Rhodus, 2012,"Treatment of Oral Candidiasis", Northwest Dentistry, 91 (2): 32-3.

(Continued)

*Primary Examiner* — Michael V Meller
(74) *Attorney, Agent, or Firm* — Harness, Dickey & Pierce P.L.C.

(57) ABSTRACT

The present invention is directed to compositions, uses and methods useful in the prevention or treatment of *Candida* infections, in particular *Candida albicans* infections and in particular recurrent *Candida* infections notably vaginal and oral or buccal candidiasis.

11 Claims, 6 Drawing Sheets

(56) References Cited

OTHER PUBLICATIONS

Slacanin et al., 1991, "Isolation and Determination of Flavonol Hlycosides from *Epilobium* Species" J. Chromatogr., 557, 391-398.
Sobel, 2007, "Vulvovaginal Candidosis" Lancet, 369 (9577): p. 1961-1971.
Sudbery et al. 2004, "The Distinct Morphogenic States of Candida Albicans" Trends in Microbiology, 12 (7), 317-324.

ANTI-CANDIDA COMPOSITIONS AND USES THEREOF

PRIORITY STATEMENT

This patent application is a U.S. national stage filing under 35 U.S.C. § 371 of International Application No. PCT/IB2015/052963 filed on 23 Apr. 2015, which claims priority to European Patent Application No. 14165729.6 filed on 24 Apr. 2014. The entire disclosures of each of the above recited applications are incorporated herein by reference.

FIELD OF THE INVENTION

The present invention relates to prevention or treatment of *Candida* infections, including *Candida albicans* infections and in particular to compositions useful for the prevention or treatment of *Candida* infections, in particular recurrent *Candida* infections notably vaginal and oral candidiasis.

BACKGROUND OF THE INVENTION

*Candida albicans* is a yeast present in mucous membranes of about 80% of human population and belongs frequently to the normal oral and intestinal flora of human.

Usually non-pathogenic, this yeast however, can become virulent in weakened organisms and may cause a fungal infection of the mucous membranes in gynecological areas called candidiasis or thrush when occurring in the mouth (James, et al., 2006, *Andrews' diseases of the skin: clinical dermatology* (10$^{th}$ ed.), Philadelphia: Saunders Elsevier. p. 308; Scully C, 2008, *Oral and maxillofacial medicine: the basis of diagnosis and treatment* (2$^{nd}$ ed.), Edinburgh: Churchill Livingstone, 191-199). About 75% of women worldwide contract once in their life vaginal candidiasis caused by *C. albicans*, and approximately 5% of women have recurrent episodes (Egan et al., 2000, *Am. Fam. Physician*, 62(5), 1095; Monif, 1985, *Am. J. Obstet. Gynecol.*, 152(7), 935; Foxman B, 1990, *Am. J. Public Health*, 80 (3), 329; Geiger et Foxman, 1996, *Epidemiology*, 7(2), 182). *Candida albicans* is carried in the mouth of about 50% of the world population as a normal component of the oral microbiota. However, when *Candida* species become pathogenic and invade host tissues, oral candidiasis may occur. This change usually constitutes an opportunistic infection of normally harmless micro-organisms due to local (i.e. mucosal), or systemic factors altering the host immunity (Kerawala et al., (editors), 2010, *Oral and maxillofacial surgery*. Oxford: Oxford University Press. pp. 446, 447); Bouquot et al., 2002, *Oral & maxillofacial pathology* (2. ed), Philadelphia: W.B. Saunders. pp. 189-197). Three main clinical appearances of candidiasis are generally recognized: pseudomembranous, erythematous (atrophic) and hyperplastic (Samaranayake, 2009, *Essential microbiology for dentistry* (3rd ed), Edinburgh: Churchill Livingstone, 178-180, 247, 293-297). The severity of oral candidiasis is subject to great inter- and intra-individual variability, and infectious episodes can be recurrent (Rhodus, 2012, "*Treatment of oral candidiasis.*". *Northwest dentistry*, 91 (2): 32-3).

Several reasons are reported to cause this infection including the use of immunosuppressive drugs, oral contraceptives, or steroids, a weakened or undeveloped immune system for example due to HIV/AIDS, mononucleosis, or metabolic illnesses like diabetes (Odds, 1987, "*Candida* infections: an overview", *Crit. Rev. Microbiol.*, 15 (1):1-5). Further conditions are linked to candidiasis such as cancer treatments, stress, pregnancy, and nutrient deficiency.

Vaginal yeast infections occur after introduction of new yeast into the vaginal area, or after increasing in the quantity of yeast already present in the vagina. The second event is often correlated to the quantity of normal bacteria. For example, when the normal, protective bacteria are eradicated by antibiotics, the yeast can multiply, invade tissues, and cause irritation of the lining of the vagina (vaginitis). Vaginal yeast infections may also occur as a result of injury to the inner vagina, such as after chemotherapy. Immunocompromised women develop also vaginal yeast infections more frequently than women with normal immunity. In extreme cases, these superficial infections of the skin or mucous membranes may enter the bloodstream and cause systemic *Candida* infections (Choo et al., 2010, *A comparative histopathological study of systemic candidiasis in association with experimentally induced breast cancer, Oncology Letters*, 1(1), p. 215-222).

Further, recurrent vulvovaginal candidiasis are quite common and difficult to treat (Ilkit et al., 2011, *Critical reviews in microbiology*, 37 (3), p. 250-61; Sobel, 2007, Lancet, 369 (9577): p. 1961-71). The reason how changes in the vagina trigger candidiasis, is unclear. It is supposed to be associated to a hormonal imbalance. In most cases, the cause of the hormonal changes is unknown. Possible risk factors have been identified including intake of antibiotics. The treatment with antibiotics can actually lead to eliminating the yeast's natural competitors for resources it often increases the severity of the condition (Bassetti et al., 2010, *Critical Care*, 14 (6), 244). *Candida albicans* possesses many virulence factors such as adhesion, biofilm formation, and morphological transformation. The first and necessary step in infection is adherence. *Candida albicans* is able of adhering to buccal, vaginal and intestinal epithelial cells as well as catheters, dental implants or artificial joints. *Candida albicans* adherence process was reported to involve a complex set of multiple mechanisms (Ollert et al., 1993, *Infect. Immun.*, 61 (11), 4560).

Furthermore, as a polymorphic organism, *Candida albicans* has the ability to grow in a variety of morphological forms. These last ones range from unicellular budding yeast to true hyphae with parallel-sided walls and, in between these two extremes, it can exhibit a variety of growth forms that are collectively referenced pseudohyphae (Sudbery et al. 2004, *Trends in microbiology*, 12 (7), 317-324; Bennett et al., 2005, *Annu. Rev. Microbiol.*, 59, 233-255). The ability to switch between yeast, hyphal and pseudohyphal morphologies is often considered to be necessary for virulence, although formal proof remains lacking.

To date, several treatments are able to stop the rapid growth of *C. albicans*. They include intravaginal treatment with creams containing miconazole or econazole, two imidazoles which inhibit the biosynthesis of ergosterol, a component of fungal membranes. However, these molecules sometimes cause side effects such as irritation to the vulva or bleeding. Oral treatments with fluconazole are said to possess the same efficiency as intravaginal treatments, but are not recommended for pregnant women. Further, fluconazole has been reported to potentially cause severe allergic skin or hepatic reactions (Rossi (editor), 2006, *Australian medicines handbook* 2006, Adelaide: Australian Medicines Handbook; FDA Drug Safety Communication, Aug. 3, 2011: *Use of long-term, high-dose Diflucan (fluconazole) during pregnancy may be associated with birth defects in infants*)

and present stability problems in water solution at ambient temperature (Dentinger et al., 2009, *Ann. Pharmacother.*, 43(3), 485-489).

The genus *Epilobium* sp. (Onagraceae) consists of about 200 species worldwide. In Europe, this genus has about 28 species. Most species are commonly known as "Willow herb". Tea and ethanolic extracts from aerial parts of this plant are used in folk medicine for the treatment of prostatic disorders, rheumatoid complaints, headache, and pain (Gruenwald et al., 2007, *Physician Desk Reference for herbal medicines*, (4$^{th}$ ed.), Montvale: Medical Economics Company, 903-4).

Therefore, there are important needs for new strategies of prevention and/or treatment of *Candida* infections, in particular recurrent *Candida albicans* infections.

SUMMARY OF THE INVENTION

The present invention relates to the unexpected finding that extracts from the species *Epilobium parviflorum* Schreb. are not only able to inhibit the growth of *Candida albicans* on vaginal epithelial cells but also to inhibit its adhesion to such cells. It is notably more surprising that other extracts from the genus *Epilobium* do not show this dual activity and that the different fractions of *Epilobium parviflorum* extracts do not share the same activity (growth inhibition/anti-adhesion). The present invention further relates to the unexpected finding that the growth inhibitory effects of *Epilobium parviflorum* extracts can be enhanced by the combination with extracts of *Artemisia annua*, which can be particularly useful in the treatment in early phase of the infection. These findings are particularly surprising that the growth inhibitory effects of *Epilobium parviflorum* extracts and *Artemisia annua* extracts are not due to the same families of active principles present in those extracts.

A first aspect of the invention provides plants of the species *Epilobium parviflorum* and/or parts of these plants and/or extracts of these plants or pharmaceutical compositions thereof for use in the prevention and/or treatment of a *Candida* infection, notably through the maintaining of skin or mucosa integrity.

A second aspect of the invention relates a use of plants of the species *Epilobium parviflorum* and/or parts of these plants and/or extracts of these plants or pharmaceutical compositions thereof for the preparation of a herbal medicine for prevention and/or treatment of a *Candida* infection.

A third aspect of the invention relates to specific *Epilobium parviflorum* extracts according to the invention.

A fourth aspect according to the invention relates to a pharmaceutical formulation comprising an extract of *Epilobium parviflorum* and at least one pharmaceutically acceptable carrier, diluent or excipient thereof.

A fifth aspect of the invention relates to a cosmetic formulation comprising an *Epilobium parviflorum* extract and at least one cosmetically acceptable carrier, diluent or excipient thereof.

A sixth aspect of the invention relates to a method of maintaining skin or mucosa integrity, notably against *Candida* infection, said method comprising contacting said skin or mucosa with an effective amount of an *Epilobium parviflorum* extract or a formulation thereof according to the invention.

A seventh aspect of the invention relates to a formulation comprising an extract of *Epilobium parviflorum*, combined with at least one co-agent useful in the prevention and/or treatment of *Candida* infections and at least one pharmaceutically or cosmetically acceptable carrier, diluent or excipient thereof. An eight aspect according to the invention comprises a method for preparing an *Epilobium parviflorum* extract comprising extracting aerial parts of dried *Epilobium parviflorum* using an alcoholic extraction or hydrolacoholic, filtering the extract of step after cooling; and concentrating the filtered extract of step b) under reduced pressure, followed by drying thereof.

DETAILED DESCRIPTION

Figure 1:
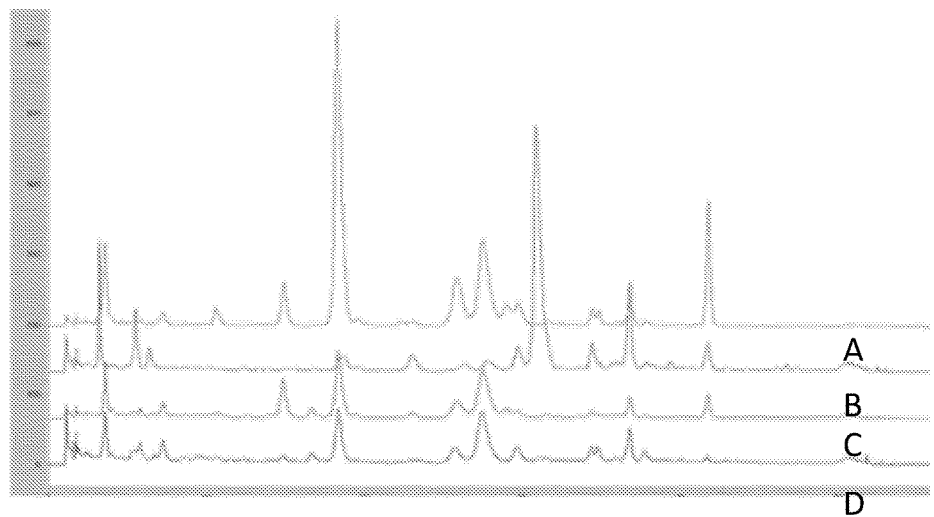
FIG. 1: HPLC Chromatogram profiles of *Epilobium* fleischeri (A), *E. angustifolium* (B), *E. dodonaei* (C) and *E. parviflorum* (D) detected at 350 nm.

The term "*Candida albicans* infections" includes cutaneous candidiasis syndromes, chronic mucocutaneous candidiasis, respiratory tract candidiasis, gastrointestinal tract candidiasis, oral thrush, hepatosplenic candidiasis and systemic candidiasis. *Candida* infections or candidiasis can be diagnosed for example by methods described in Ellepola et al., 2005, *J. Microbiol*, 43(S), 65-84; Avni et al., 2011, *J. Clin. Microbiol.*, 49(2): 665-670.

The term "*Candida*" includes *Candida albicans*, *Candida krusei*, *Candida tropicalis*, *Candida glabrata*, and *Candida parapsilosis*.

The "smallflower hairy willowherb" is often misused on the market and wrongly assigned, especially in the case of products allegedly containing *E. parviflorum* (Kiss et al., 2011, *Phytomedicine*, 18(7), 557-560). The term "*Epilobium parviflorum*" according to the invention refers to *Epilobium* with small flowers and includes consequently willowherbs issued from the section *Epilobium* L., in particular the *Epilobium* sp., *Epilobium parviflorum*, *Epilobium tetragonum*, *Epilobium montanum*, *Epilobium alpinum*, and *Epilobium lanceolatum*.

The term "vaginal delivery system" includes vaginal solutions for the intimate hygiena, capsules and tablets containing the extract of *Epilobium parviflorum*, and optionally probiotics of the species *Lactobacillus*, for a local delivery in the vagina or in the mouth as well as delivery systems and applicator systems that allow suitable delivery of the formulations of the invention in the vagina and allow the formulation to stay at the site of action for sufficient time for efficiency. According to one aspect, vaginal delivery systems include mucoadhesive vaginal drug delivery systems such as described for example in Acartfırk, 2009, *Recent Patents on Drug Delivery & Formulation* 2009, 3(3), 193-205 or in Ashok et al., 2012, *Critical Review in Pharmaceutical Sciences*, 1(1), 1-19, which contents are incorporated herein in its entirety.

The term "pharmaceutically acceptable" refers to a carrier comprised of a material that is not biologically or otherwise undesirable.

The term "cosmetically acceptable" refers to a carrier comprised of a material that is not biologically or otherwise undesirable for topical use on the skin or mucosa.

The term "carrier" refers to any components present in a pharmaceutical formulation other than the active agent and thus includes diluents, binders, lubricants, disintegrants, fillers, coloring agents, wetting or emulsifying agents, pH buffering agents, preservatives and the like.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and is not necessarily meant to imply cure or complete abolition of symptoms, but refers to any type of treatment that imparts a benefit to a patient and includes: (a) preventing the disease from occurring in a subject which may be predisposed to the disease but has not yet been diagnosed as having it for example based on familial history, overweight status or age; (b) inhibiting the disease, i.e. arresting its development; or relieving the disease, i.e. causing regression of the disease and/or its symptoms or conditions such as improvement or remediation of damage.

In particular, prevention and/or treatment of *Candida* infections according to the invention comprise decreasing sensitivity of an individual to *Candida* infections and in particular to recurrent *Candida* infections. For example, it comprises maintaining the skin or mucosa integrity or preventing the *Candida* adhesion on said skin or mucosa surface. The term "treatment" refers to any type of treatment or prevention that imparts a benefit to a subject afflicted with or at risk of developing *Candida* infections, including improvement in the condition of the subject (e.g., in one or more physiological conditions) or slowing the progression of infection, etc.

According to one aspect, effects of a treatment or application according to the invention may be observed through reduction of the symptoms of candidiasis such as itching, burning, soreness, irritation, and a whitish or whitish-gray cottage cheese-like discharge (Watson et al., 2007, *Aust. N New Zealand J. Obstet. Gynaecol.*, 47 (4), 262-272). The term "efficacy" of a treatment, application or method according to the invention can be measured based on the number of *C. albicans* measured using sterile swab which has been used to rub on the infected skin surface. The swab is streaked on a culture medium which is then incubated at 37° C. for several days, to allow development of yeast or bacterial colonies. The characteristics, such as morphology and colors, of the colonies allow diagnosis of candidiasis.

Extracts

The extracts according to the invention are extracted by standard methods such as those referred in Doughari, 2012, *Phytochemicals: extraction methods, basic structures and mode of action as potential chemotherapeutic agents, phytochemicals—a global perspective of their role in nutrition and health*, Toronto: Dr Venketeshwer Rao; Ong 2004, *J. Chromatogr. B. Analyt. Technol. Biomed Life Sci.*, 812(1-2), p. 23-33; Abbet et al., 2014, *Food Chemistry*, 160 (1), 165-170. Plant extracts according to the invention may be extracted by using water or alcohols, in particular low alcohols (such as ethanol, n-butyl alcohol), or a mixture thereof as a solvent. An example of alternative method includes extraction in a glycerol or water/glycerol solution.

The extraction method is accelerated solvent extraction (ASE), percolation, self-immersion extraction, ultrasonic extraction and circumfluence extraction such as described in EP 1767212. For instance, extraction can be obtained in mixed solvent of ethanol-water such as for example at a volume ratio: 90:10 to 10:90, in particular mixed solvent of ethanol-water at a volume ratio: 30:70 or pure ethanol.

According to one aspect, the extract according to the invention is prepared by a method comprising the following steps:
  a) extracting aerial parts of dried *Epilobium parviflorum* using an extraction solvent, in particular by accelerated solvent extraction in ethanol;
  b) filtering the extract of step a) after cooling; and
  c) concentrating the filtered extract of step b) under reduced pressure, followed by drying thereof.

In a particular embodiment, a therapeutically or prophylactically effective amount of an extract of *Epilobium parviflorum* may be from about 0.25 to about 8 mg/ml dry matter weight, in particular from about 0.25 to about 1 mg/ml. According to a particular embodiment, a therapeutically or prophylactically effective amount of an extract of *Epilobium parviflorum* may be from about 0.5 mg/ml to about 5 mg/ml. These may be characterized by the percentage of dry matter which they contain. Dry matter is the solid residue remaining after removal of the carrier or solvent by drying, such as by drying a solution or suspension in an oven, by lyophilization or evaporation under vacuum. Dry matter may be expressed in % and may also be referred to as plant solids concentration. Thus, a 100 g or 100 mL solution or suspension containing 5% dry matter by weight, yields 5 grams of solids or residue after drying. Alternative methods of drying may yield slightly different values for the percent by weight of dry matter, so that all such values recited herein are necessarily approximations. Dry matter values include suspended as well as settled solids. The dry matter values of the extracts of the invention have been determined according to The European Pharmacopoeia $8^{th}$ edition, chapter 2.8.17.

Compositions

According to one aspect, the invention provides a composition containing a plant extract from *Epilobium parviflorum*.

According to a further aspect, the plant extract from *Epilobium parviflorum* is from aerial parts of *Epilobium parviflorum*.

According to another further aspect, the plant extract from *Epilobium parviflorum* is from the leaves.

According to another further aspect, the plant extract further comprises a plant extract from *Artemisia annua*. In a particular embodiment, the plant extract from *Artemisia Annua* is from aerial parts of the plant source.

According to another further aspect, the plant extract from *Epilobium parviflorum* is a hydroalcoholic or alcoholic plant extract or an aqueous plant extract.

In another particular embodiment, the invention provides a composition comprising an *Epilobium parviflorum* extract for use as a medicament.

In another particular embodiment, the invention provides a pharmaceutical formulation comprising an *Epilobium parviflorum* extract and at least one pharmaceutically acceptable carrier, diluent or excipient thereof.

In another particular embodiment, the invention provides a cosmetic formulation comprising an *Epilobium parviflorum* extract and at least one cosmetically acceptable carrier, diluent or excipient thereof.

According to a further embodiment, the invention provides a cosmetic formulation according to the invention comprising from about 0.25 to about 4.00 mg/ml of an *Epilobium parviflorum* extract and at least one cosmetically acceptable carrier, diluent or excipient thereof.

In another particular embodiment, the invention provides an *Epilobium parviflorum* extracts of the invention, wherein the extract is an alcoholic or hydroalcoholic extract.

In another particular embodiment, the invention provides an *Epilobium parviflorum* extracts of the invention, wherein the extract is a glycerol extract.

In another particular embodiment, the invention provides an *Epilobium parviflorum* extracts of the invention, wherein the extract is an ethanol or ethanol-water extract.

In another particular embodiment, the invention provides a formulation of the invention wherein the formulation is a liquid or semi-solid formulation such as a gel or hydrogel.

The invention provides *Epilobium parviflorum* extracts, pharmaceutical compositions thereof, and methods for treating a subject, in particular a mammalian subject, and most particularly a human patient who is suffering from or at risk of suffering a *Candida* infection, in particular a *Candida albicans* infection.

Compositions of the invention contain at least one *Epilobium parviflorum* extract according to the invention in any form described herein. Compositions of this invention may further comprise one or more pharmaceutically acceptable additional ingredient(s) such as alum, stabilizers, antimicrobial agents, buffers, coloring agents, flavoring agents, adjuvants, and the like.

The compositions according to the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for topical use.

According to the invention, the compositions of the invention may be prepared in the form of a gel for oral hygiene or for application to the human skin or mucosal surfaces, in the form of toothpaste, in the form of a cream for application to the skin, or a liquid formulation for mouth rinsing or washing the human mucosal surfaces or skin and/or for application to the skin.

According to the invention, the compositions of the invention may be prepared in the form of solid form (capsule, tablets) for gastrointestinal infections.

According to the invention, the compositions of the invention may be prepared in the form of a foam, a cream, a gel, a jelly, a moisturizer, a spray, a suppository, a vaginal capsule, a vaginal tablet, a vaginal film, a vaginal sponge, a vaginal ovule or any other vaginal health product such as a liquid solution for the intimate hygiene. The composition may also be applied to a vaginal insert, tampon, wipe or pad. The composition may further include a suitable diluent and/or excipient.

Compositions of this invention may be liquid formulations including, but not limited to, aqueous or oily suspensions, solutions, emulsions. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate, dehydroacetic acid, benzyl alcohol, and sorbic acid.

Dispersing or wetting agents include, but are not limited to, poly(ethylene glycol), glycerol, bovine serum albumin, Tween®, Span®, Sodium cocoyl glutamate, Disodium cocoyl glutamate, *Quillaja saponaria* wood extract, Caprylyl/capryl glucoside.

According to a further embodiment, compositions of the present invention may further comprise other pharmaceutically acceptable further excipient, including mucoadhesive excipients and suitable excipient to maintain proper viscosity of formulation. Mucoadhesive excipients include cellulose polymers, such as carboxymethylcellulose, hydroxypropyl methylcellulose, methylcellulose, hydroxyl ethyl cellulose, ethyl cellulose and the like, alone or in combination, gelatin, colloidal anhydrous silica or polyacrylic acid derivative polymers, such as carbomers, polycarbophils and the like. In a particular aspect, mucoadhesive excipients possess gel-forming properties.

According to a further embodiment, compositions of the present invention may further comprise at least one lipophilic excipient. Lipophilic excipients sinclude glyceryl stearates and derivatives, for example, polyethylene glycol stearates, ketostearyl alcohols, polyoxyethylene glycol ethers of n-alcohols (lauryl, cetyl, stearyl and myristyl alcohol), liquid paraffin, lecithin oil, glycerol and the like.

According to a further embodiment, compositions of the present invention may further comprise hydrating agents such as Seabuckthorn juice and *Aloe barbadensis* leaf juice.

According to a further embodiment, compositions of the present invention may further comprise soothing agents such as *Anthemis nobilis* flower water, *Malva officinalis* extract and *Leontopodium alpinum* extract.

According to a further embodiment, compositions of the present invention may further comprise disinfecting or antiseptic agents such as *Anthemis nobilis* flower water, *Malva officinalis* extract, *Alchemilla vulgaris* extract.

According to a further embodiment, compositions of the present invention may further comprise emollient agents such as *Malva officinalis* extract.

According to a further embodiment, compositions of the present invention may further comprise pH regulating agent such as lactic acid.

Further materials as well as formulation processing techniques and the like are set out in Part 5 of *Part 5 of Remington's "The Science and Practice of Pharmacy", 22$^{nd}$ Edition,* 2012, University of the Sciences in Philadelphia, Lippincott Williams & Wilkins the content of which is incorporated herein by reference.

Mode of Administration

Extracts and compositions of this invention may be administered in any manner including topical, intra-vaginal and intra-buccal.

The exact dose of extracts and compositions is readily determined by one of skill in the art based on the teachings herein, along with the potency of the extract and composition, the age, weight, sex and physiological condition of the subject.

According to one embodiment, *Epilobium parviflorum* extracts and compositions of the invention are applied or administered before or at the beginning of the onset of the *Candida* infection symptoms or when at risk of a *Candida* infection.

According to another embodiment, *Epilobium parviflorum* extracts and compositions of the invention are applied or administered after the onset of the *Candida* infection, in particular in the phase which follows the luminal *Candida* growth phase. According to a further embodiment, *Epilobium parviflorum* extracts and compositions of the invention applied or administered in combination with *Artemisia annua* extracts.

Combinations

According to the invention, extracts according to the invention and pharmaceutical formulations thereof can be administered alone or in combination with a co-agent useful in the prevention and/or treatment of *Candida* infections, in particular agents useful for regeneration of mucosal flora e.g. for example a co-agent selected from probiotics like the *Lactobacillus* strains (for example *Lactobacillus helveticus*) or further plant extracts such as described herein.

According to a particular aspect, is provided a formulation according to the invention, wherein the co-agent useful in the prevention and/or treatment of *Candida* infections or in the maintaining of skin or mucosa integrity is a probiotic, in particular *Lactobacillus*, more particularly *Lactobacillus helveticus*.

According to a further particular embodiment, the probiotic, in particular *Lactobacillus*, more particularly *Lactobacillus helveticus* is administered at a dose ranging from about $10^8$ cfu/ml to about $10^{10}$ cfu/ml in the composition.

According to a particular aspect, is provided a formulation according to the invention comprising 0.25 to about 2.00 mg/ml of an *Epilobium parviflorum* extract to be used in combination with a probiotic, in particular *Lactobacillus*, more particularly *Lactobacillus helveticus* at a dose from about $10^8$ cfu/ml to about $10^{10}$ cfu/ml.

The invention encompasses the administration of extracts according to the invention and pharmaceutical formulations thereof to an individual prior to, simultaneously or sequentially with other therapeutic/prophylactic regimens or co-agents in the prevention or treatment of *Candida* infections or in the maintaining of skin or mucosa integrity. An extract or the pharmaceutical formulation thereof that is administered simultaneously with said co-agents can be administered in the same or different composition(s) and by the same or different route(s) of administration.

The dosage administered, as single or multiple doses, to an individual will vary depending upon a variety of factors, including pharmacokinetic properties, patient conditions and characteristics (age, body weight, health, size), extent of symptoms, concurrent treatments, frequency of treatment and the effect desired.

Patients

In an embodiment, patients according to the invention are patients suffering from a *Candida* infection.

In another embodiment, patients according to the invention are patients at risk of suffering from *Candida* infection.

Patients at risk of suffering from *Candida* infection include patients suffering from recurrent *Candida* infections, patients with suppressed immune systems, diabetic patients, patients under treatment with cortisone-related medications and pregnant patients.

Use According to the Invention

According to one aspect, the invention provides plants of the species *Epilobium parviflorum* and/or parts of these plants and/or extracts of these plants or pharmaceutical compositions thereof for use in the prevention and/or treatment of a *Candida* infection.

In one embodiment of the invention, is provided a use of a plant of the species *Epilobium parviflorum* and/or parts of these plants and/or extracts of these plants or a formulation thereof according to the invention for the preparation of a pharmaceutical composition for the prevention, repression and/or treatment of a *Candida* infection.

In another embodiment of the invention is provided a method for preventing and/or treating a *Candida* infection in a subject, said method comprising administering in a subject in need thereof an effective amount of a *Epilobium parviflorum* extract or a formulation thereof according to the invention.

In another embodiment of the invention is provided a method for preventing *Candida* adhesion on mucous membrane, said method comprising contacting said mucous membrane with an effective amount of an *Epilobium parviflorum* extract or a formulation thereof according to the invention.

In another embodiment of the invention is provided a method for maintaining skin or mucosa integrity, said method comprising contacting said skin or mucosa with an effective amount of an *Epilobium parviflorum* extract or a formulation thereof according to the invention.

According to another embodiment, the invention relates to a pharmaceutical formulation comprising an *Epilobium parviflorum* extract, combined with at least one co-agent useful in the prevention or repression of a *Candida* infection, and at least one pharmaceutically acceptable carrier, diluent or excipient thereof.

In another embodiment, is provided a composition, a use or a method according to the invention, wherein the *Epilobium parviflorum* extract or a composition thereof is to be used in combination with at least one co-agent useful in the prevention or repression of a *Candida* infection.

In another embodiment, is provided a medicinal kit comprising in compartmental form a first compartment or series of compartments comprising *Epilobium parviflorum* extract or a compositions thereof such as for example in a form of an ovule or capsule and optionally a second compartment or series of compartments comprising an applicator and/or further composition for vaginal use, in a form of an ovule or capsule such as probiotic compositions, with instructions for use.

In another embodiment, is provided a vaginal delivery system comprising a composition according to the invention and optionally an applicator.

In another embodiment, is provided a buccal or mouth rinsing solution comprising a composition according to the invention.

In a further embodiment, the *Candida* infection is a *Candida albicans* infection.

In another further embodiment, the *Candida* infection is a vaginal *Candida* infection.

In another further embodiment, the *Candida* infection is a mouth or buccal *Candida* infection.

In another aspect, the *Candida* infection is a gastrointestinal *Candida* infection such as characterized for example by *Candida* overgrowth and even a *Candida* penetration of the gastrointestinal mucosa.

Extracts, uses and methods according to the invention are particularly useful in the prevention of *Candida* infections, in particular *Candida albicans* infections, notably recurrent vaginal and oral *Candida albicans* infections. Those extracts, uses and methods according to the invention present not only the advantage to prevent growth of the yeast but also to prevent its adhesion to the mucosa which is mostly responsible of recurrence. In addition, uses and methods according to the invention provide the advantage to avoid the use of fungicide treatments which increase the risk of resistance.

According to another aspect, extracts and compositions according to the invention used in the gentle cleansing lotion or solutions, for example in daily personal hygiene, have the advantages to contribute to maintain skin and mucosa integrity.

Examples illustrating the invention will be described hereinafter in a more detailed manner and by reference to the embodiments represented in the Figures.

EXAMPLES

The following abbreviations refer respectively to the definitions below: ASE (accelerated solvent extraction), cfu/mL (colony-forming units per milliliter); DMEM (Dulbecco's Modified Eagle's medium), DMSO (dimethylsulfoxide), EDTA ((Ethylenedinitrilo)tetraacetic acid), EGF (Epideramal growth factor), FCS (foetal calf serum), HEPES ((4-(2-hydroxyethyl)-1-piperazineethanesulfonic acid), PBS (Phosphate buffer saline), SDA (Sabouraud Dextrose Agar), SFM (serum free medium).

Example 1

Compared Activities Between Different *Epilobium* Species and Between Different Methods of Extraction Different plant extracts from the *Epilobium* sp. were compared in view of their inhibitory activity on *C. albicans* growth and adhesion.

Plant Extraction

Plant extraction was run on the four species *Epilobium parviflorum, E. angustifolium, E. fleischeri* and *E. dodonaei* (syn. *E. rosmarinifolium*). Powders were extracted following one of the following procedures:

a) Extraction in Water (at 100 Bars, 80° C.)

The dried aerial parts are milled with an ultracentrifugal mill (Retsch ZM100) with 1 mm Conidur sieve. Plant material was extracted by accelerated solvent extraction (ASE), with demineralized water (80° C., 1 extraction cycle of 5 minutes). The extract was precipitated with L-lactic acid PhEur (Fluka Analytical, 69775) (mass ratio crude extract ratio to acid lactic of 150:1). The mixture is cooled at 4° C. for 24 hours and then centrifuged at 1500 rpm during 10 minutes. The supernatant is harvested and filtered with 0.2 µm filter. The content of dried matter is adjusted to 5% using rotary evaporation and glycerol (Hanseler AG, 07-3800.01) is added to a final content of 40%. The extract was filtered with 0.2 µm filters under sterile conditions and stocked in 1 ml vials at −20° C.

b) Extraction in Ethanol (EtOH, 30% at 100 Bars, 40° C.)

The dried aerial parts are milled with an ultracentrifugal mill (Retsch ZM100) with 1 mm Conidur sieve. Plant material was extracted by accelerated solvent extraction (ASE), with water-ethanol (7:3 vol./vol.), (40° C., 1 extraction cycle of 5 minutes). The extract was concentrated by rotary evaporation in order to standardize the final content of dried matter to 5% in the final solvent of extract, ethanol or glycerol. The extract was filtered with 0.2 µm filters under sterile conditions and stocked in 1 ml vials at −20° C.

HPLC-DAD Analyses

The extracts were analyzed by HPLC-DAD (Hewlett Packard 1090 series II) and detected at 350 nm using a reverse phase column (CC 250/3 Nucleosil 100-5 C18 HD; serie n° N9070717, batch n° 20418032) with a gradient of acetonitrile (LAB-SCAN analytical sciences, C73C11X) and formic acid 0.1% at 1.0 ml/min. The resolution of the chromatograms allowed the differentiation of the different *Epilobium* species as shown on FIG. 1.

Inhibitory Activity on *Candida* Growth

The effects of those *Epilobium* extracts were tested on *Candida albicans* growth as follows:

Culture Preparation

*Candida albicans* cells (ATCC MYA-2876) were incubated in SB (Sabouraud broth, Biolife 4020002) for 24 h at 30° C. and 150 rpm. The obtained culture was enumerated with a Neubauer Improved count chamber and concentration adjusted to $2.5 \cdot 10^3$ cfu/ml by dilution with sterile SB. Vaginal cells (End1/E6E7, ATCC CRL-2615) have been grown in Keratinocyte SFM (Gibco 17005-42) with 0.1 ng/ml human recombinant EGF (Gibco 10450-013), 0.05 mg/ml bovine pituitary extract (Gibco 13028-014) and additional calcium chloride 44.1 mg/L according to instructions by the provider, with media change every 2-3 days.

*Candida* Growth Test

Minimal inhibitory concentration (MIC) of the plant extracts and antifungal substances was accomplished through tissue culture plates of 96 wells with flat bottom (Becton Dickinson). In each well 100 µl of the $2.5 \cdot 10^3$ cfu/ml *Candida albicans* culture obtained as described above in SB was mixed with 100 µl plant extract of different concentrations (0.025, 0.083, 0.25, 0.83, 2.5 and 8.3 mg/ml). Together with each dilution series a blank well was prepared with 100 µl culture and 100 µl of 5% ethanol-water solution. Fluconazole (Sigma, F8929) has been taken as positive control. Fluconazole solutions of different concentrations (4, 16, 32, 65, 650 µg/ml) have been freshly prepared prior testing. A well with only broth (100 µl) plus water (100 µl) and a well with broth plus plant extract (100 µl) were also prepared for color control. The plate was then incubated at 37° C. for 24 h and 48 h.

Evaluation of the Results

Figure 2:
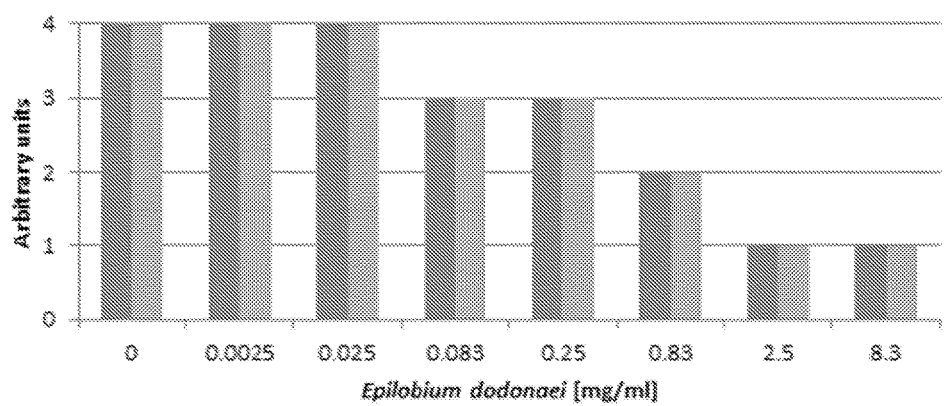
FIG. 2: Inhibitory activity on *Candida albicans* growth as measured according to Example 1 expressed in arbitrary units based on visual observation criteria as described below after 24 h (□) and 48 h (■) of incubation. A: *E. dodonaei*; B: *Epilobium fleischeri*; C: *E. parviflorum* and D: *E. angustifolium*.
Figure 2:
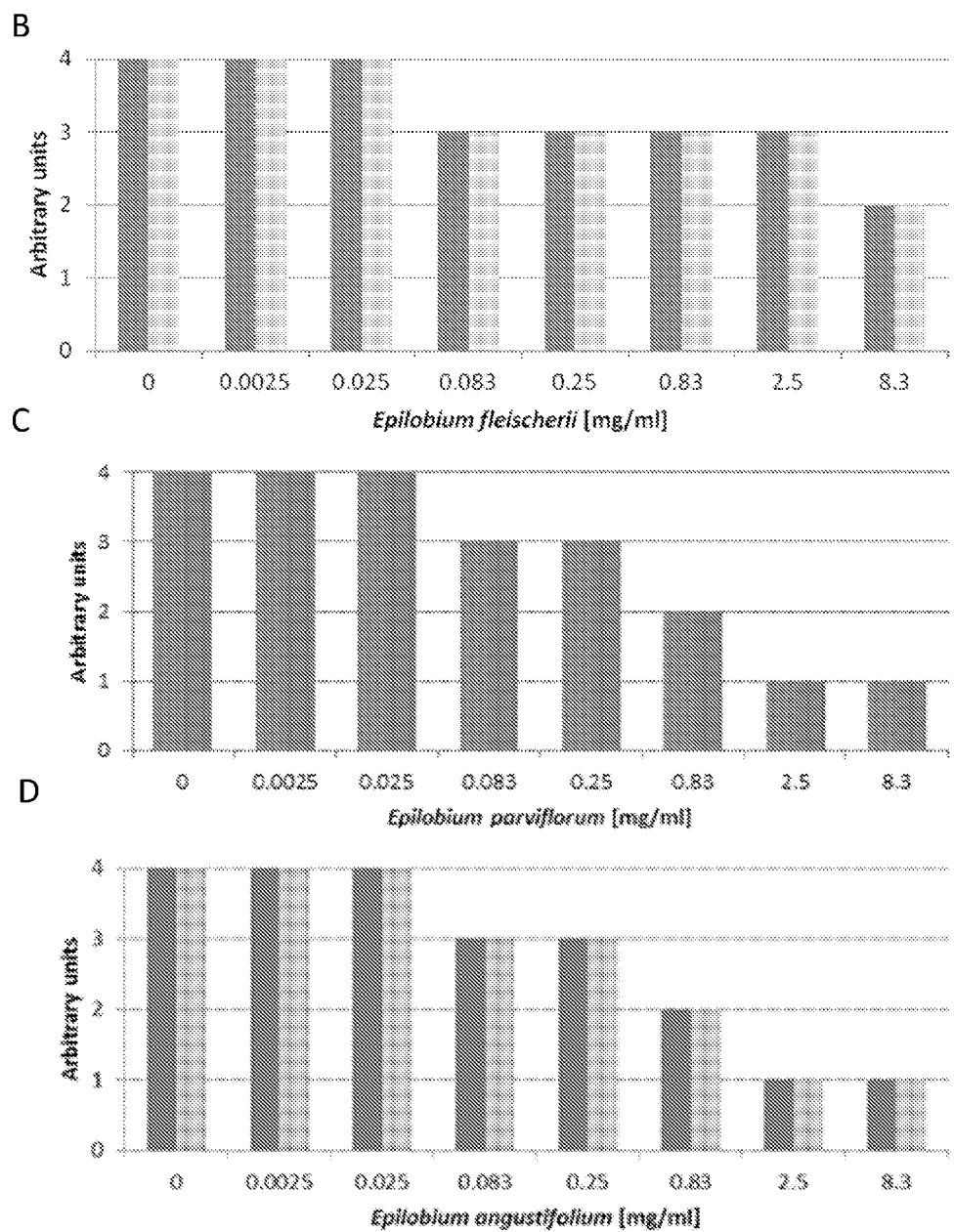

The evaluation of the growth inhibitory activities was conducted by visual observation of the turbidity of the wells and by attribution of a score from 0 (no growth) to 4 (maximal growth, similar to control well). MIC value of a substance is defined as the concentration which permits to reach a score of less than 4. It has to be noticed that a score of 2 does not indicate a 50% diminution of *Candida* concentration but indicates a turbidity of the well with half the intensity compared to the one of the control well. In fact, the score of 2 represents an inhibition of *Candida* concentrations of about 80%. Results are presented on FIG. 2.

Effect of Fluconazole

Fluconazole inhibited *Candida* growth to a similar degree by all 5 concentrations applied. Fluconazole seems to be more effective if used fresh, indicating a weak stability issue of fluconazole in aqueous solution which is consistent with the literature (Dentiger et al., 2009, supra). Therefore, the inhibition of *Candida* growth was less effective after 48 h incubation with fluconazole than after 24 h, despite still showing a significant inhibition of *Candida* growth (arbitrary unit of 2 to 3 like shown from 2 separate runs).

Inhibitory Activity on *Candida* Adhesion

The effects of those *Epilobium* extracts were tested on *Candida albicans* adhesion as follows:

A tissue culture plate of 24 wells was prepared with vaginal epithelial cells. 0.5 ml of a culture of $10^5$ cells/ml in keratinocyte SFM were put in each well of a 24-well plate and incubated for 2 days at 37° C. and 5% $CO_2$. Each well was filled (after taking away the vaginal cells growth media) with 1 ml *C. albicans* culture of $5 \cdot 10^6$ cfu/ml mixed with test substance. As control, the solvent of each test substance was also tested. The plate was incubated at 37° C. for 6 h or 2 h (5 h for Example 2, 2 h for Example 4), permitting *Candida* cells to adhere to vaginal cells. After incubation the *Candida* culture was pipetted away from each well, which were then washed 3 times with 0.5 ml PBS. The epithelial cells-*Candida* layer was treated with a 0.05% trypsin solution (concentration of 1 ml/25 $cm^2$), which was then neutralized by addition of DMEM with 10% FCS. Cells were scraped from plastic with appropriate scrapers and one supplementary wash step. The obtained cell solution was diluted and analyzed with pour plate method (*Manuel Suisse des denrées alimentaires, Chapitre* 56, 2000, revision partielle 2004): 1 ml of the appropriate dilution was pipetted into an empty Petri dish and about 15-20 ml of SDA, cooled down to 45-50° C., poured over it.

Figure 3:
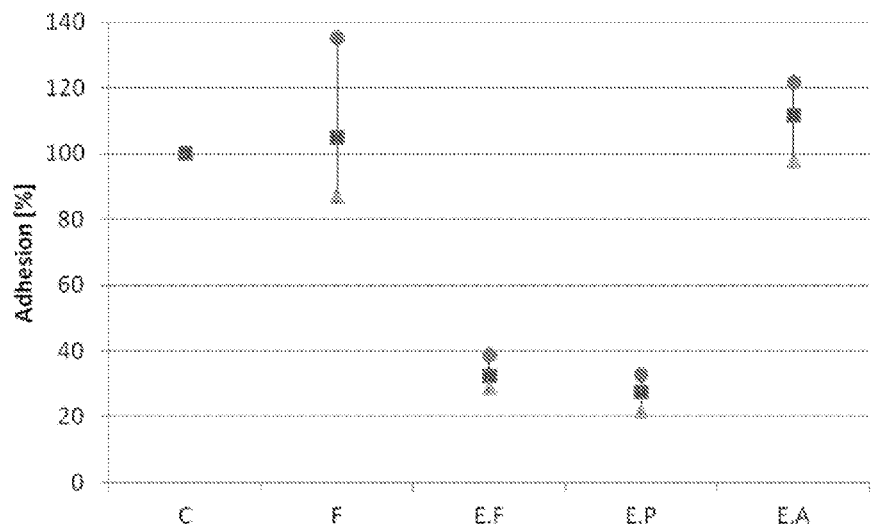
FIG. 3: Inhibitory activity on *Candida albicans* adhesion on human vaginal epithelial cells as measured according to Example 1 at 5 mg/ml for the *Epilobium* extracts and at 1 mg/ml for fluconazole, after 6 hour incubation. Each sample has been analysed 5 times. Average values (■), highest values (●), lowest values (▲) are represented. Adhesion was analysed after 6 hours of co-culturing and extracts were added at the beginning of the adhesion. Reference sample (C), is a 0.5% ethanol solution instead of plant extract, was taken as 100% adhesion which represent about $2.10^6$ cfu/ml. E.F.: *E. fleischeri*, E.P.: *E. parviflorum* and E.A.: *Epilobium angustifolium*.

After 24 h incubation at 37° C. the colonies were counted and the result (in cfu/ml) multiplied 1.5 times to obtain the number of adhered cell in each well. Adhesion was expressed in %, given that 100% was adhesion in absence of inhibitor. Results are presented in FIG. 3.

Effect of *Epilobium* Extracts on *Candida* Growth

*Epilobium dodonaei* inhibited *Candida* growth. The $MIC_{50}$ value has been observed at a concentration of 0.83 mg/ml. Concentration ranging from 2.5 mg/ml to 8.3 mg/ml do inhibit growth even stronger. Only a weak inhibitory effect is manifested at concentrations of 0.083 mg/ml to 0.250 mg/ml, and no effect could be seen at concentrations lower than 0.025 mg/ml. The extract has shown a constant effect over a period of 48 hours, as no differences in growth could be seen after 24 h and 48 h of treatment.

*Epilobium fleischeri* was the less efficient among the three *Epilobium* extracts that were tested. The $MIC_{50}$ value of 8.3 mg/ml represented the tested concentration with the strongest inhibition. No difference was seen in a concentration range of 0.083 mg/ml up to 2.5 mg/ml, concentrations which resulted only in a weak inhibition. As for the other extracts, concentrations below 0.025 mg/ml did not have an effect.

*E. dodonaei, E. parviflorum* and *E. angustifolium* have similar inhibitory effects on *Candida* growth. The three of them have a $MIC_{50}$ value of 0.83 mg/ml and best inhibition results with concentrations of 2.5 and 8.3 mg/ml. *E. fleischeri* is less effective and has a $MIC_{50}$ value which is 10 times higher than the other extracts (8.3 mg/ml). The stability of the growth inhibition effect after 24 h, and lasting for at least 48 h, was constant for all 4 extracts. However, the respective effect of fluconazole was shorter, showing maximal effect at 24 h and reduced effects at 48 h. Therefore, the *Candida* inhibitory effect of the *Epilobium* extracts seems longer-lasting than the existing treatment with fluconazole.

Effect of *Epilobium* Extracts on *Candida* Adhesion

Comparing to control sample, fluconazole did not have an inhibition effect on *Candida* adhesion, as average value remained at 100%. A certain variability of the *Candida* counts was observed in the presence of fluconazole.

*E. Angustifolium* at 5 mg/ml was not Able to Inhibit Adhesion of *Candida*.

*E. parviflorum* and *E. fleischeri* at 5 mg/ml both showed significant inhibitions of adhesion when compared to other *Epilobium* extracts and the control. Adhesion amounted to around 30% for both, meaning that the extracts inhibit adhesion by about 70%. Variability of values is low in both cases.

No detachment of the epithelial monolayer was observed, neither in absence of extracts nor in their presence, therefore, the fact that the lack of adhesion may be due to lack of vaginal cell viability was discarded.

In conclusion, plant extracts of *Epilobium* inhibit more efficiently adhesion of *Candida* to human epithelial cells when compared to the drug fluconazole.

Altogether, those data support the fact that, depending on the species from genus *Epilobium*, the *Epilobium* extracts have different effects on *Candida* growth and adhesion. *E. parviflorum* extracts present unexpected combined effects on both *Candida* growth and adhesion that are not exhibited by the other *Epilobium* extracts. Further, *E. parviflorum* extracts prevent an anti-adhesion effect that fluconazole does not have.

Example 2

Effects of Combinations of *Epilobium parviflorum* Extracts and *Artemisia annua* Extracts The effects of a mixture of *Epilobium parviflorum* and *Artemisia annua* extracts on *Candida albicans* adhesion were tested as follows:

Plant Extraction

The dried aerial parts of *Artemisia annua* and *Epilobium parviflorum* were milled separately with an ultracentrifugal mill (Retsch ZM100) with 1 mm Conidur sieve. They were mixed homogeneously together to a mass ratio of 1:1. The mixture was extracted by accelerated solvent extraction (ASE) following the procedure described in Example 1.

Samples of *A. annua* and *E. parviflorum* extracts were prepared according to the pharmacopoeia (European Pharmacopoeia 7.0, chap. 2.8.14). Only the step of the treatment with skin hide (FILK GmbH, Freiberg, Germany, 350 400) and the filtration step is performed. The obtained filtrate is standardized following the procedure described in Example 1. A monitoring by HPLC-DAD showed that molecules eluting between 3 and 5 minutes with UV maxima at 217 nm and 265 nm are no more present in the filtrate. Those extracts were tested and compared to *A. Annua* and *E. parviflorum* extracts obtained without skin hide (tannins not removed).

Inhibitory Activity on *Candida* Growth

The effect of a mixture of *A. Annua* and *E. parviflorum* extracts in equal proportions was tested on the growth of

*Candida albicans* according to the method described in Example 1. The antifungal substance fluconazole was used as positive control.

Inhibitory Activity on *Candida* Adhesion

The effect of a mixture of *A. Annua* and *E. parviflorum* extracts in equal proportions was tested on the adhesion of *Candida albicans* according to the method described in Example 1. The antifungal substance fluconazole was used as positive control.

Screening of Human Cytotoxicity

Potential cytotoxicity of the extracts was assayed in the neutral red-screening test using human vaginal epithelial cells at 80% confluence corresponding to $2*10^5$ cells per well of 96 wells as follows:

The extracts freshly extracted and stored once frozen were incubated for 24 h with the epithelial cells at different concentrations. At the end of the experiment the cells were washed 3× and incubated with Neutral Red (NR) medium (50 µg/ml) for 3 hours at 37° C., 5.0% $CO_2$/air. A water solution at 0.5% ethanol was used as negative control (present in all samples). As positive control and validation component SDS was diluted and run in parallel resulting in $IC_{50}$=8-25 µg/ml. Cells were then washed and NR quantified. 100% staining intensity indicate intact lysosomal activity. 0% indicates little to no survival of human cells. Results were analysed according to the Hill function. $IC_{50}$ or concentrations with highest impairment of cell survival were determined.

Figure 4:
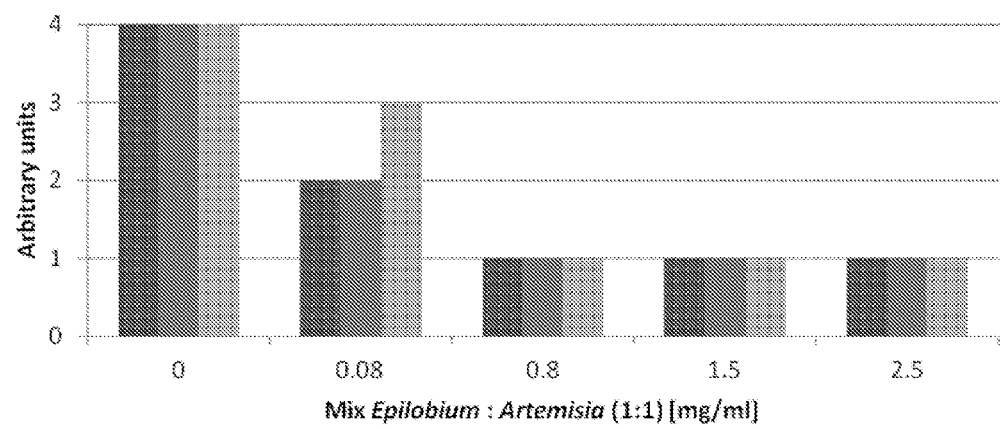
FIG. 4: Inhibitory activity on *Candida albicans* growth as measured according to Example 2 expressed in arbitrary units after 18 h (■), 24 h (■) and 48 h (■) of incubation. A: mix of *Artemisia annua* and *Epilobium parviflorum* extracts in equal proportions; B: *Artemisia annua* extract alone and C: tannins-depleted *Artemisia annua* extract alone.
Figure 4:
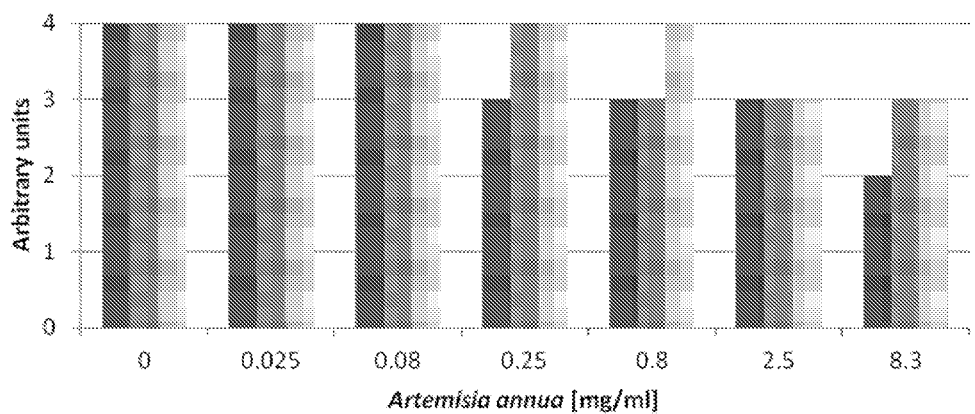
Figure 4:
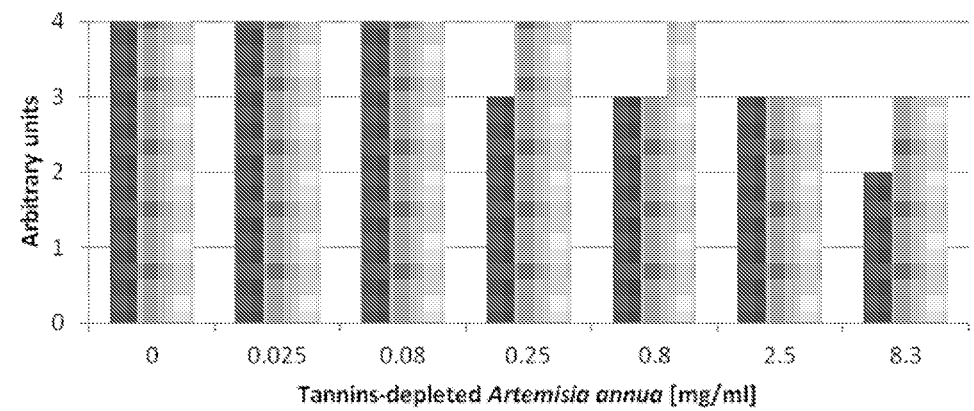

Desorb solution was prepared in a ratio of water-ethanol-acetic acid glacial (49:50:1; v:v) during 20 min with shaking. Wavelength used for spectrophotometric reading of NR optical density was 540 nm. Test Criteria were that the differences between VC mean; R2>0.85; Point >0%<100%. The results are presented on FIG. 4.

Effects of the Mixture *Artemisia:Epilobium* on *Candida* Growth

The *Artemisia:Epilobium* extracts mix inhibits growth of *Candida* effectively at concentrations ranging from 0.8 to 2.5 mg/ml. The effect remains consistent for 48 h. The lowest concentration tested of 0.08 mg/ml is less effective, but still shows a good inhibition of growth after 18 h and 24 h (arbitrary unit of 2). After 48 h the observed effect at 0.08 mg/ml has diminished.

*Epilobium parviflorum* extract alone potently inhibited *Candida* growth at concentrations of 0.8 mg/ml and higher. The effect was constant throughout 48 h. At concentrations between 0.08 mg/ml and 0.25 mg/ml growth inhibition was lower. The effect remains constant for 48 h at 0.25 mg/ml, whereas it diminished at 48 h at 0.08 mg/ml. Even at 0.025 mg/ml *Epilobium* inhibited growth of *Candida*. As opposed, the *E. parviflorum* extract, when depleted of the tannins, did not have any inhibitory effect on *Candida* growth. Only at 8.3 mg/ml and after 18 h there was a moderate effect, which however disappeared after 24 h. Therefore, the *Epilobium*'s tannins play an important role in *Candida* growth inhibition.

Inhibition of *Candida* growth by *Artemisia* extract alone was less efficient than the inhibition with *E. parviflorum* extract alone, since the effect of the *Artemisia* extract was first detectable at 0.8 mg/ml at 24 h while the effect of the *E. parviflorum* extract was detectable at 0.025 mg/ml. *Artemisia annua* extract had an effect on *Candida* growth at 8.3 mg/ml after 18 h, which diminished after 24 h and 48 h. Between concentrations of 0.25 mg/ml and 2.5 mg/ml there is an inhibitory effect, which however disappeared after 48 h. At 2.5 mg/ml the effect lasted for 48 h. The effect on *Candida* growth by tannin-depleted *Artemisia annua* extract was however identical to the one by the whole *Artemisia annua* extract.

Therefore *Artemisia*'s tannins are different from those in *E. parviflorum*. Furthermore, it supports that tannins and polyphenols are not alone responsible for *Candida* growth inhibition activity of *Artemisia annua* extract.

Effects of the Mixture *Artemisia-Epilobium* on *Candida* Adhesion

The effect of a mix of *A. Annua* and *E. parviflorum* extracts in equal proportions was tested on the adhesion of *Candida albicans* to human epithelial cells as described above. Average adhesion of *Candida* in presence of *A. Annua* extract alone was 73% and adhesion in presence of *A. Annua* extract without tannins was 87%. Average adhesion of *Candida* in presence of *E. parviflorum* extract alone was 5% and adhesion in presence of *E. parviflorum* extract without tannins was >100%. Average adhesion of *Candida* in presence of *A. Annua* plus *E. parviflorum* mix extract (M=mix) was <5%. Therefore, the mix of *Epilobium* and *Artemisia* was highly efficient in preventing adhesion of *Candida* to human epithelial cells, although extracts of *E. parviflorum* alone at 5 mg/ml were already preventing adhesion efficiently.

Different concentrations (5 mg/ml, 0.5 mg/ml and 0.05 mg/ml) of a mixture of *Artemisia annua* and *Epilobium parviflorum* have been analyzed on adherence inhibition of *Candida albicans* to human epithelial cells as described above. A dose response effect was seen with different concentrations of an *Artemisia annual*Epilobium parviflorum* extract mixture. For an extract (mix) concentration of 5 mg/ml the adhesion of *Candida* to vaginal cells lied at 5%, indicating an almost total inhibition effect of the mix. For a concentration of 0.5 mg/ml adhesion was at 30% and for 0.05 mg/ml adhesion was at 70%. Therefore, the plant extract mix were highly inhibitory at 5 mg/ml, still more than half-maximal inhibitory at 0.5 mg/ml and, although less inhibitory, still active at 0.05 mg/ml (about 40% inhibition).

Altogether, those results support that the inhibition of *Candida* growth is more efficient when *Epilobium parviflorum* extracts are combined with *Artemisia annua* extracts compared to *Epilobium parviflorum* extracts or with *Artemisia annua* extracts alone and the mechanisms of action of both extracts are different and thus complementary. Such combination might be especially useful in the treatment at early attack phase of the infection.

Example 3

Compared Activities of *Epilobium parviflorum* Extracts Obtained by Different Methods

*Epilobium parviflorum* extracts obtained by different processes were tested for their ability to inhibit adhesion of *Candida albicans* to human epithelial cells as described in Example 2 at 5 mg/ml.

Extraction in Ethanol 30% (100 Bars, 40° C.) (Extract 1)

This extraction method was used as described in Example 1.

Extraction in Water 100% (100 Bars, 80° C.) with Precipitation with Lactic Acid at 4° C. and Stabilization with Glycerol (Extract 2)

This extraction method was used as described in Example 1. The supernatant (sng), the sediment (solid) and the whole extracts were all tested.

Extraction in Ethanol (EtOH, 98% at 100 Bars, 40° C.) (Extract 3)

This extraction method was used as described in Example 5.

Results are presented in Table 3 below as compared to Pepstatine A (Carl Roth 2936, Germany) (at 1 µM) which is a known inhibitor for adhesion inhibiting aspartic proteases and in turn *Candida* adhesion to human epithelial cells (Ollert et al., 1993, supra).

TABLE 3

| *Epilobium parviflorum* extract | % inhibition |
|---|---|
| Extract 1 | 95 (at 5 mg/ml) |
| Extract 2 (sng) | 25 to 65 depending on the *Epilobium* source (at 0.5 mg/ml) |
| Extract 3 | 88 (at 0.25 mg/ml) |
| Pepstatin A | 5 (at 1 µM) |

Those data support the fact that the anti-adhesion activities between the different *Epilobium parviflorum* extracts obtained by different extraction methods are retained. The supernatant of the *Epilobium parviflorum* extract (extract 2) seems to have the strongest anti-adhesion effect as compared to the sediment and whole extract and the extract obtained by extraction in ethanol at 98% seems to preserve high anti-adhesion activity even at concentrations as low as 0.25 mg/ml. The commercial inhibitor Pepstatine A has a very low inhibitory activity as compared to the tested extracts.

Example 4

Identification of the Fractions in *Epilobium parviflorum* Extracts and Activities Thereof The extract of *E. parviflorum* was submitted to a HPLC-based activity profiling as described below. Each fraction was tested on the previously described established in-vitro cell-based assay. This approach aimed to characterize natural fractions endowed with anti-adhesive properties or acting as growth-inhibitors.

Extractions and Fractionation

The dried aerial parts (20 g) were ground using a ZM 1 ultracentrifugal mill (Retsch, Haan, Germany), with 1 mm Conidur sieve. To target the potential polar active ingredients, the plant material was first macerated in 160 g of hexane during 4 hours. After filtration, the plant residue is again extracted with 160 g of a mixture of water-ethanol-n-butanol (1:1:1) during 4 hours. After filtration, the extract is evaporated to get 2 phases (40° C., 100 mbar). Formic acid is added to the aqueous phase until reaching a pH of 3. The aqueous fraction is partitioned with n-butanol (2×50 mL). The butanolic fraction are recovered and evaporated to dryness.

Fractionation

Figure 5:
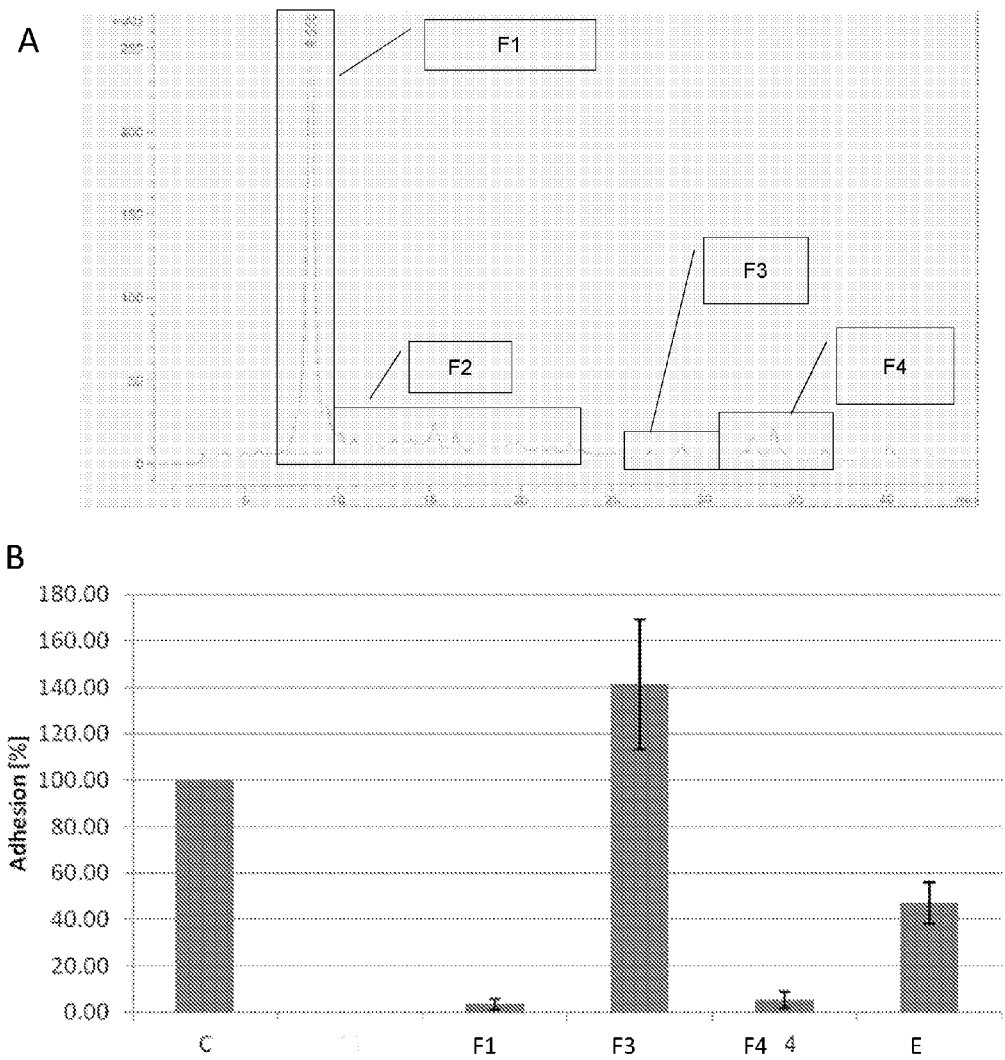
FIG. 5: Repartition of the fractions of *Epilobium parviflorum* extracts as described in Example 4 (A) and their inhibitory activity on *Candida albicans* adhesion on human vaginal epithelial cells as measured according to Example 1 after 2 hour incubation (B): C: only water; F1: fraction 1 from *Epilobium parviflorum* extract at 5% dried matter; F3: fraction 3 from *Epilobium parviflorum* extract at 5% dried matter; F4: fraction 4 from *Epilobium parviflorum* extract at 5% dried matter and E: whole *Epilobium parviflorum* extract at 5% dried matter.

The residue is dissolved in 15 mL of a methanol 30% solution and fractionation was performed on a medium-pressure-liquid-chromatography (MPLC) coupled to a UV detector Knauer 2500 (Knauer, Germany). Detection was at 280 nm. Four fractions were obtained as shown in the FIG. 5. Phytochemical investigations revealed the major presence of oenothein B (>64%) in fraction 1 (F1), and of different flavonols including myricetin and quercetin derivatives in fraction 4 (F4). Phytochemical characterization of the two other fractions was not achieved due to the too low amount of materials.

Inhibitory Activity on *Candida* Growth and on *Candida* Adhesion

Fractionation of *Epilobium* extracts showed that the fraction 1 (F1) corresponding to 1% of the dried plant weight, with a high amount of oenothein B (>64%) reduced adhesion to 3.5% at a final concentration of 1 mg/mL of oenothein B, whereas Fraction 4 (F4) reduced the adhesion to 5%. The control inhibition with whole *Epilobium* extract 5% dried matter (1/10 final) resulted in 47% adhesion in the same test.

Fraction 1 inhibits the most the growth of yeast (>95%) whereas for fractions 3 and 4 the inhibitory activity was less important (>60%, and 20% respectively). Interestingly, the fraction 3 (F3), which exhibited a high inhibitory activity on *Candida albicans* growth, did not show any anti-adhesion activity, whereas Fraction 4 (F4) reduced the adhesion to 5%.

The control inhibition with whole *Epilobium* extract 5% dried matter (1/10 final) resulted in 47% adhesion in the same test.

The observed effects are particularly unexpected and cannot be simply attributed to a relative high content in oenothein B of those extracts. According to Ducrey et al., 1997, *Planta Med*, 63(2), 111-114 the different measured amounts in oenothein B in several species of *Epilobium* lead to the conclusion that *E. parviflorum* and *E. angustifolium* contained similar amounts of oenothein whereas *E. dodonaei* showed 2 to 3 times more oenothein B (Ducrey et al., 1997, supra). As shown in Example 1, the effects of extracts from those three species were similar on yeast growth, but extracts from *E. angustifolium* were not able to inhibit its adhesion.

Further, several authors determined that the myricitrin was the most abundant flavonoid in *E. parviflorum*, whereas *E. angustifolium*, which belongs systematically to the section *Chamaenerion Tausch.*, showed a complete other flavonoid pattern from other *Epilobium* species: instead of having myricitrin as the main constituent, isoquercitrin was identified as the most abundant flavonoid (Slacanin et al., 1991, *J. Chromatogr.*, 557, 391-398; Ducrey et al., 1995, *Phytochemistry*, 38(1), 129-137).

*E. dodonaei* contains flavonoid profile similarities with both species namely *E. angustifolium* and *E. parviflorum*, whereas flavonoid pattern of *E. fleischeri* seems to be closer to the one of *E. parviflorum* (Ducrey, 1995, supra; Wichtl (editor), *Herbal drugs and Phytopharmaceuticals* (3$^{rd}$ ed.), Stuttgart: medpharm GmbH Scientific Publishers, p. 193).

In conclusion, fractionation of *Epilobium parviflorum* extracts of the invention showed that the presence of high polar substances such as oenothein B led to interesting properties in growth inhibition of the yeast, whereas the more lipophilic fraction containing different flavonoids showed weak growth inhibition but strong anti-adhesion properties. These data corroborate the results obtained in the Example 2, wherein the alcoholic or hydroalcoholic extracts showed a better anti-adhesion effect than aqueous extract.

The results suggest that the effects of *Epilobium parviflorum* extracts of the invention do not only depend on their growth inhibitory properties, but may also be strengthened by their antiadhesion properties. Therefore, those data support that different fractions of *Epilobium parviflorum* extracts of the invention have advantageous complementary effects on the inhibition of growth and/or adhesion of *Candida albicans*.

Example 5

Example of Combination of *Epilobium* Extracts and *Lactobacillus*

Combinations of a plant extract according to the invention with probiotic bacteria were tested for their anti-adhesion effect on *Candida albicans* on human vaginal cells.

Extraction of *Epilobium* and Preparation of the Sample

The dried plant aerial parts were powdered under liquid nitrogen with A1M20 universal mill (IKA WERKE, Stausen, Germany). 2.5 g of dried plant material were extracted by pressurized liquid extraction (PLE), with ethanol 98% (40° C., 3 extraction cycles of 5 minutes). Solvent was removed under reduced pressure. The dried extract was stored in the dark at 4° C. and was put in solution (dried extract was dissolved in a small quantity of DMSO and filled up to the desired volume with PBS). The obtained extract was sterile filtered (0.2 µm) prior to use. The final concentration of DMSO is of 3.3% which is further diluted to 0.3% or 0.03% for ADH tests) for MIC test and ADH test. 37.5 mg of the obtained extract have been mixed with 50 µl of DMSO and phosphate-buffered saline (PBS) containing 8 g/L NaCl, 0.2 g/L KCl, 1.44 g/L $Na_2HPO_4$ and 0.24 g/L $KH_2PO_4$ has been added to reach a final volume of 1.5 ml. The extract was then sterile filtered (0.2 µm). Further dilutions in PBS have been made for adhesion tests.

MIC Test Culture Preparation

*Candida albicans* cells (ATCC MYA-2876) were incubated in SB (Sabouraud broth, Biolife 4020002) for 24 h at 30° C. and 150 rpm. The obtained culture was enumerated with a Neubauer Improved count chamber and concentration adjusted to $5 \cdot 10^3$ cfu/ml by dilution with sterile SB.

Probiotic bacteria *Lactobacillus* LAFTI (from Institut Rosell-Lallemand) cells were incubated in MRS-Broth for 24 h at 37° C. The obtained culture was enumerated with a Neubauer Improved count chamber and concentration adjusted to $5 \cdot 10^3$ cfu/ml by dilution with sterile MRS-B.

Growth Test

Minimal inhibitory concentration (MIC) of the extracts was determined on tissue culture plates of 96 wells with flat bottom (Becton Dickinson). In each well 100 µl of the $5 \cdot 10^3$ cfu/ml *Candida albicans*/*Lactobacillus* LAFTI culture in SB/MRS-B was mixed with 100 µl plant extract of different concentrations. The solvent used for extract preparation (3.3% DMSO in PBS) was diluted in the same way as the extracts and each dilution tested to make sure that DMSO is not responsible for a possible growth inhibition. A well with only broth (100 µl) plus PBS (100 µl) and a well with broth plus the different dilutions of plant extract (100 µl) were also prepared for color control. For negative control the antibacterial substance Cloramphenicol (20 mg/L) and the antifungal substance pimaricin (20 mg/L) were tested. The plate was then incubated at 37° C. for 24 h.

Evaluation of the Results

The evaluation was conducted by visual observation of the turbidity of the wells and by attribution of a score from 0 (no growth) to 4 (maximal growth, similar to control well). $MIC_{50}$ value of a substance is defined as the concentration which permits to reach a score of 2. It has to be noticed that a score of 2 does not indicate a 50% diminution of bacterial/fungal concentration but indicates a turbidity of the well with half the intensity compared to the one of the control well.

*Epilobium parviflorum* extracts completely inhibited growth of *Lactobacillus* LAFTI grown in solution (MRS Broth), at concentrations of 16 and 8 mg/ml, but not at 4 mg/ml and lower. Therefore, in the following adhesion experiments a concentration of 2 mg/ml *Epilobium parviflorum* extracts was added to the co-culture of *Candida albicans*, *Lactobacillus* LAFTI and human cells. The medium used in the ADH co-culture was DMEM (which is a sub-optimal medium for *Lactobacillus* LAFTI growth, yet allowing its survival).

As main read-out of the adhesion experiments, the interaction of *Candida* to human cells was quantified in presence and absence of the treatment. Treatments were applied at different combinations of LAFTI and *Epilobium parviflorum* extracts, and at different time points of the 2 h *Candida* infection.

Adhesion Test Culture Preparation

*Candida albicans* cells were incubated in SB for 24 hours at 30° C. After incubation the cell number of the culture was counted under the microscope with a Neubauer Improved count chamber. A *Candida* concentration of $5.5 \cdot 10^6$ cfu/ml has been mixed with the test substance (9 parts culture+1 part test substance).

*Lactobacillus* LAFTI was incubated in MRS-B for 24 h at 37° C. The culture was enumerated and the desired amount centrifuged 2 min at 4,000 g. The final concentration of *Lactobacillus* LAFTI in the culture has to attain $10^9$ cfu/ml.

Vaginal cells (End1/E6E7, ATCC CRL-2615) have been grown in Keratinocyte SFM (Gibco 17005-42). 0.5 ml of the $10^5$ cells/ml culture has been put in each well of a 24-well plate. The plate has been incubated for 48 h at 37° C. and 5% $CO_2$.

Adhesion Test

Each well was filled with 1 ml *C. albicans* culture of $5 \cdot 10^6$ cfu/ml mixed with test substance. As control, the solvent of each test substance was also tested. The plate was incubated at 37° C. for 2 h, permitting *Candida* cells to adhere to vaginal cells. After incubation the *Candida* culture was pipetted away from each well. Cells were scraped from plastic with appropriate scrapers and one supplementary wash step was done with 0.5 ml PBS. The obtained solution was diluted and analyzed with pour plate method on SDA (Sabouraud Dextrose Agar, Biolife 4020052).

After 24 h incubation at 37° C. the colonies were counted and the result (in cfu/ml) multiplied 1.5 times to obtain the number of adhered cell in each well. Adhesion was expressed in %, given that 100% was adhesion in absence of inhibitor.

A concentration of 0.25 mg/ml *Epilobium parviflorum* extract was tested in presence and absence of $1.10^9$ cfu/ml *Lactobacillus* LAFTI. Also the extract alone and an extract –LAFTI mix were added after 30 min of *Candida*-vaginal cells preincubation, to evaluate whether the extract and probiotics have an effect on already adhered *Candida* cells.

Adhesion of *Candida* in presence of 0.25 mg/ml *Epilobium parviflorum* extract accounts to 12.4%±1.5% ($\alpha$=5%). The same sample in presence of about $1.10^9$ cfu/ml of probiotics gives a much lower adhesion value of 0.98%±0.24%.

Similarly, for samples where the treatment was added after 30 min of *Candida* incubation there is a difference between *Epilobium parviflorum* extract alone and *Epilobium parviflorum* extract LAFTI mix. The addition of *Epilobium parviflorum* extract alone results in an adhesion of 73.2%±11.4%, whereas the addition of the *Epilobium parviflorum* extract –LAFTI mix in adhesion of 32.6%±7.0% (both samples were compared to the same control sample). Therefore, those data support that the *Epilobium parviflorum* extract +LAFTI sample has a stronger effect than *Epilobium parviflorum* extract alone in detaching already adhering *Candida*.

Those results support that probiotics have a synergistic effect and strengthen the anti-adhesion efficacy of the *Epilobium parviflorum* extract.

Example 6

Example of Gel Formulations and Activity Thereof

A personal hygiene composition according to the invention comprising an *Epilobium parviflorum* extract according to the invention and the following additional ingredients: Aqua, *Anthemis nobilis* flower water, *Aloe barbadensis* leaf juice, decyl glucoside, glycerin, *Hippophae ramnoides* fruit juice, *Quillaja saponaria* wood extract, *Hippophae rhamnoides* fruit extract, *Alchemilla vulgaris* extract, *Malva officinalis* extract, sodium cocoyl glutamate, disodium cocoyl glutamate, maltodextrin, dehydroacetic acid, benzyl alcohol, lactic acid, pH 4.0-5.0 has been prepared.

The effects of the personal hygiene composition referenced above are flowed by an observational study conducted by a gynaecologist on 15 women suffering from recurrent vaginal candidiasisis. The personal hygiene composition is used once a day for three weeks. Significant reduction of burning sensation, dryness, irritations, and itching are observed at the end of the study.

Example 7

Effect of an Extract of the Invention on *C. albicans* Adhesion on Buccal Host Cells

*Epilobium parviflorum* extracts of the invention were tested for their ability to inhibit adhesion of *Candida albicans* to buccal cells as follows:

*Candida albicans* cells were incubated in SDB for 24 hours at 30° C. and 150 rpm. A fraction of this culture (1 ml) was then incubated in NB (Nutrient Broth, Biolife 401815) with 5 g/L yeast extract (Biolife 4122202) for 18 h at 30° C. without rotation. After incubation the cell number of the culture was counted under the microscope with a Neubauer Improved count chamber. An adequate quantity of the second *Candida* culture was put into a falcon tube and centrifuged (Universal 32R, Attich Zentrifugen) 2 min at about 4000 g. The pellet has been washed 3× with phosphate-buffered saline (PBS) containing 8 g/L NaCl, 0.2 g/L KCl, 1.44 g/L $Na_2HPO_4$ and 0.24 g/L $KH_2PO_4$ and with final pH 7.3 and then resuspended in DMEM media (with HEPES) containing 0.1 ng/ml EGF and $CaCl_2$ (0.4 mM final concentration). The culture quantity taken for centrifugation and the DMEM media added to cell pellet has to be calculated as to have a final culture concentration of $5.5 \times 10^6$ cfu/ml. The obtained *Candida* culture in DMEM has been mixed with the test substance (9 parts culture+1 part test substance). Buccal cells (TR146, cell line human, ECACC) have been grown in Hams F12 (Life Technologies 31765-027)+10% FCS+2 mM L-glutamine. Cells grown in a T75 have been washed with PBS and treated with 3 ml of a trypsine 0.05% –EDTA solution (5 min at 37° C. and 5% $CO_2$). After complete detachment of cells, 12 ml of growth media have been added and cells counted. The culture has been centrifuged 5 min at about 110 g and pellet resuspended in growth media to obtain a culture of $1 \times 10^5$ cells/ml. 0.5 ml of the $1 \times 10^5$ cells/ml culture has been put in each well of a 24-well plate. The plate has been incubated for 48 h at 37° C. and 5% $CO_2$.

A tissue culture plate of 24 wells was prepared with buccal cells prepared as described above. Each well was filled with 1 ml *C. albicans* culture of $5 \cdot 10^6$ cfu/ml mixed with the test substance (*Epilobium parviflorum* extract of the invention obtained in the same conditions as in Example 5 at 0.25 mg/ml). As control, the solvent of each test substance was also tested. The plate was incubated at 37° C. for 2 h, permitting *Candida* cells to adhere to buccal cells. After incubation the *Candida* culture was pipetted away from each well, which were then washed 3 times with 0.5 ml PBS.

Figure 6:
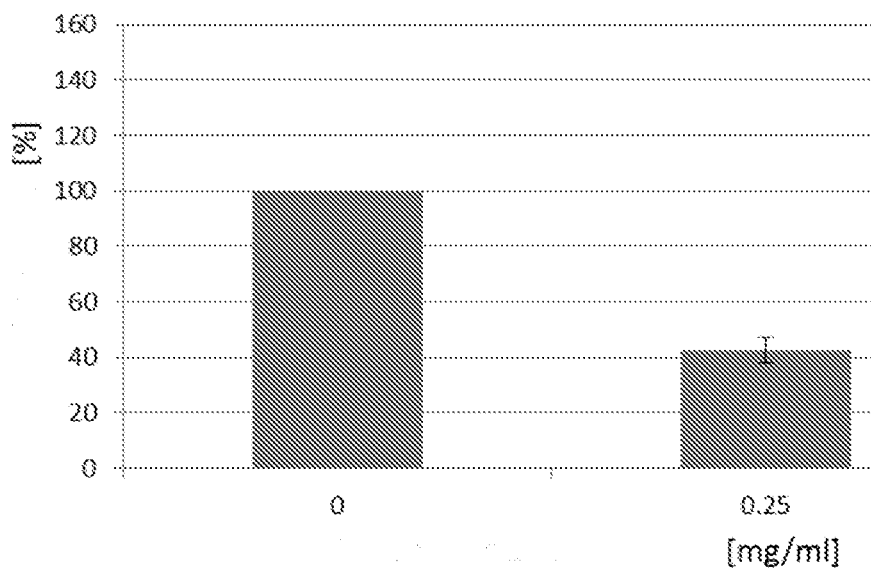
FIG. 6: Inhibitory activity on adhesion of *Candida albicans* on human buccal epithelial cell-layer after incubation for 2 h as described in Example 7, in absence (o mg/ml) and presence of a fresh, raw extract of *E. parviflorum* (0.25 mg/ml) obtained as described in Example 5. Average value of 4 measures and confidence interval at 95% is shown.

The epithelial cells-*Candida* layer was treated with a 0.05% trypsin solution (concentration of 1 ml/25 $cm^2$) for 1 min. 9 volumes of neutralization medium with serum were added to neutralize the action of trypsin. Cells were scraped from plastic with appropriate scrapers and one supplementary wash step was done with 0.5 ml PBS. Standard solution and wash buffer were collected in the same Eppendorf tube and centrifuged at about 1260 g for 1 min (Galaxy 14D, VWR). The supernatant was thrown away and fresh 1.5 ml PBS added. The obtained solution was diluted and analyzed with pour plate method on SDA (Sabouraud Dextrose Agar, Biolife 4020052). After 24 h incubation at 37° C., the colonies were counted and the result (in cfu/ml) multiplied 1.5 times to obtain the number of adhered cell in each well. Adhesion was expressed in %, given that 100% was adhesion in absence of inhibitor. The results are presented under FIG. 6 and show that 0.25 mg/ml an *E. parviflorum* extract of the invention significantly inhibited *C. albicans* adhesion, resulting in 40% of the maximal adhesion rate. 100% adhesion accounted to the adhesion in the absence (0 mg/ml) of *E. parviflorum*. Those data support that the extracts of the invention are also able to inhibit adhesion on buccal cells.

Example 8

Effect of an Extract of the Invention on *C. albicans* Adhesion on Caco-2 Cells

*Epilobium parviflorum* extracts of the invention are tested for their ability to inhibit adhesion of *Candida albicans* to gastrointestinal cells as follows:

*Candida albicans* cells are prepared as described in Example 7. Intestinal cells Caco-2 (ATCC CRL-2102) are grown in DMEM advanced with 2 mM L-glutamine, 10% FCS and PenStrep until confluence of about 80%, washed with PBS and treated with a trypsine 0.05% –EDTA solution (1 ml/25 cm2) for 5 min at 37° C. and 5% $CO_2$. After complete detachment of cells, action of trypsine is neutralized with growth media and the culture is centrifuged 5 min at about 110 g. Cell pellet has to be resuspended in growth media for cell count. A $1 \times 10^5$ cells/ml culture is prepared and 0.5 ml of it is put in each well of a 24-well plate. The plate is incubated for 48 h at 37° C. and 5% $CO_2$. A tissue culture plate of 24 wells is prepared with intestinal cells prepared as described above. Each well is filled with 1 ml *C. albicans* culture of $5 \cdot 106$ cfu/ml mixed with test substance (*Epilobium parviflorum* extract of the invention). Control, incubation conditions and intestinal cells-*Candida* layer treatment are the same as under Example 7.

The invention claimed is:
1. A method of treating a *Candida albicans* infection in a human in need thereof, the method comprising administering a therapeutically effective amount of an *Epilobium parviflorum* extract or a formulation of an *Epilobium parvi-*

*florum* extract to the human in need thereof to effectively treat the *Candida albicans* infection in the human in need thereof.

2. A method according to claim 1, wherein the extract is an extract of the aerial parts of *Epilobium parviflorum*.

3. A method according to claim 1, wherein the extract is to be used in combination with a plant extract from *Artemisia annua*.

4. A method according to claim 1, wherein the therapeutically effective amount of the *Epilobium parviflorum* extract or the formulation of the *Epilobium parviflorum* extract is administered topically, intra-vaginally or intra-buccally to the human in need thereof.

5. A method according to claim 1, wherein the *Candida* infection is a vaginal *Candida albicans* infection.

6. A method according to claim 1, wherein the *Candida* infection is an oral or buccal *Candida albicans* infection.

7. A method according to claim 1, wherein the *Candida* infection is a gastrointestinal *Candida albicans* infection.

8. A method according to claim 1, wherein the extract is an alcoholic or hydroalcoholic extract.

9. A method according to claim 1, wherein the extract is obtained by accelerated solvent extraction in ethanol.

10. A method according to claim 1, wherein the formulation of the *Epilobium parviflorum* extract comprises about 0.25 to about 1 mg/ml of *Epilobium parviflorum* extract.

11. A method according to claim 1, wherein the *Epilobium parviflorum* extract is administered in combination with a probiotic.

\* \* \* \* \*